United States Patent [19]

Weeks

[11] Plant 4,706

[45] May 5, 1981

[54] ROSE PLANT

[76] Inventor: O. L. Weeks, 4759 Philadelphia St., Chino, Calif. 91710

[21] Appl. No.: 142,179

[22] Filed: Apr. 21, 1980

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Vincent G. Gioia

[57] ABSTRACT

A new hybrid tea rose variety of unusual yellow ochre-orange buff coloring, with visible petal veining grown on a healthy, vigorous plant.

1 Drawing Figure

1

The present invention relates to a new and distinct variety of rose plant of the hybrid tea rose class, which was originated by my crossing as seed parent an unnamed, unreleased seedling of my creation and the rose known as "Oldtimer" as pollen parent.

Among the novel characteristics possessed by this new variety which distinguish it from its parents and all other varieties of which I am aware are the unusual coloring of the flowers, borne primarily singly, and the vigor and health of the plant which is unusual for varieties of this coloring. Asexual reproduction by budding of the new variety as performed in San Bernardino County, Calif., shows that the foregoing and other distinguishing characteristics come true to form and are established and transmitted through succeeding propagations.

The new and improved rose variety which I have developed is an unusual hybrid tea rose with blooms of good hybrid-tea form displayed on a vigorous upright, free branching plant with abundant disease resistant foliage. The flowers are of medium petalage with a distinctive color development. Originating as a nasturtium orange bud, the flower opens and matures to yellow-ochre and orange buff coloring, lightening only slightly upon aging.

The seed and pollen parents though of somewhat similar general coloring differ in tonality and color development and significantly in plant growth and vigor. The new variety is more robust, vigorous and larger growing than its parents.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.

*Seed parent.*—Unnamed, unpatented and unreleased seedling.

*Pollen parent.*—"Oldtimer".

Class: Hybrid tea.

2

The following observations are made of specimens grown outdoors in San Bernardino County, Calif., during the month of October.

FLOWER

Blooming habit: Intermittent to continuous.

A. *Bud.*—(1) Size: Medium. (2) Form: Ovoid. (3) Color: When sepals first divide — 25C. When petals begin to unfurl — 22B to 22C with some minor occasional reddish tint at petal edge. (4) Sepals: Simple, somewhat foliated, about same length as bud. (5) Peduncle: Length — medium. Aspect — straight, almost smooth. Strength — erect. Color — 138A.

B. *Bloom.*—(1) Size: Average size when fully expanded — about 4 to 4½-inches. (2) Borne: Singly and in small clusters. (3) Form: Fairly high centered, begins relatively flat and appears more high centered at ⅓ open. (4) Petalage: Number of petals under normal conditions — about 29. (5) Color: Nasturtium orange bud lightens to orange buff and at about ⅓-open predominant color is between yellow ochre 22A and orange buff 22B. The underside of petals is near 24B but includes some vague reddish tone. Top side of petal is lighter colored amber yellow 18A. Thus, as flower opens and matures overall color effect is from near 24B to 18A and aged bloom is Indian yellow 17D. Fully open blooms may be a combination of the foregoing colors. Veining, noticeable in partially opened blooms, continues to be evident as flower matures.

C. *Petals.*—(1) Texture: Thick. (2) Appearance: Velvety to satiny. (3) Form: Obovate, petals quill to pronounced point. (4) Arrangement: Regularly arranged. (5) Petaloids in center: Few. (6) Persistence: Drop off cleanly. (7) Fragrance: Slight. (8) Lasting quality: Long lasting on plant and as cut flower.

REPRODUCTIVE ORGANS

A. Stamens, filaments and anthers:

(1) *Arrangement.*—Many stamens regularly about pistils, short to long filaments.

(2) *Color.*—Yellow.

B. Pollen: Color — gold yellow.

C. Styles: Very short, bunched.

D. Stigmas: Color — yellowish brown.

E. Hips: None observed.

PLANT

A. Form: Upright.

B. Growth: Vigorous, free branching.

C. Foliage: Compound 3 to 5 leaflets.

(1) *Size.*—Medium.

(2) *Quantity.*—Abundant.

(3) *Color.*—New foliage: Upper side — near to 178A with green. Under side — near to 178A with green. Old foliage: Upper side — 136A. Under side — 139C.

(4) *Shape.*—Mucronate.

(5) *Texture.*—Upper side is moderately glossy and under side is dull.

(6) *Edge.*—Serrated.

(7) *Serration.*—Simple.

(8) *Leaf stem.*—Color — near to 137C. Under side — 137C.

(9) *Stipules.*—Medium.

(10) *Resistance to disease.*—Mildew — good. Rust — good.

D. Wood:

(1) *New wood.*—Color — near 137C with reddish tone. Bark — smooth, shiny.

(2) *Old wood.*—Color — near 138A. Bark — smooth, shiny.

E. Thorns:

(1) *Thorns.*—Quantity (main stalk): Ordinary. On laterals from stalk — few. Form — recurved tip. Length — medium. Color — tan. Position — scattered.

(2) *Prickles.*—Few.

F. Winter hardiness: Good winter hardiness.

I claim:

1. A new and distinct variety of rose plant of the hybrid tea class, substantially as shown and described, characterized particularly by its unusual yellow ochre-orange buff flower coloring, blooms borne on a robust, vigorous plant and attractive green foliage.

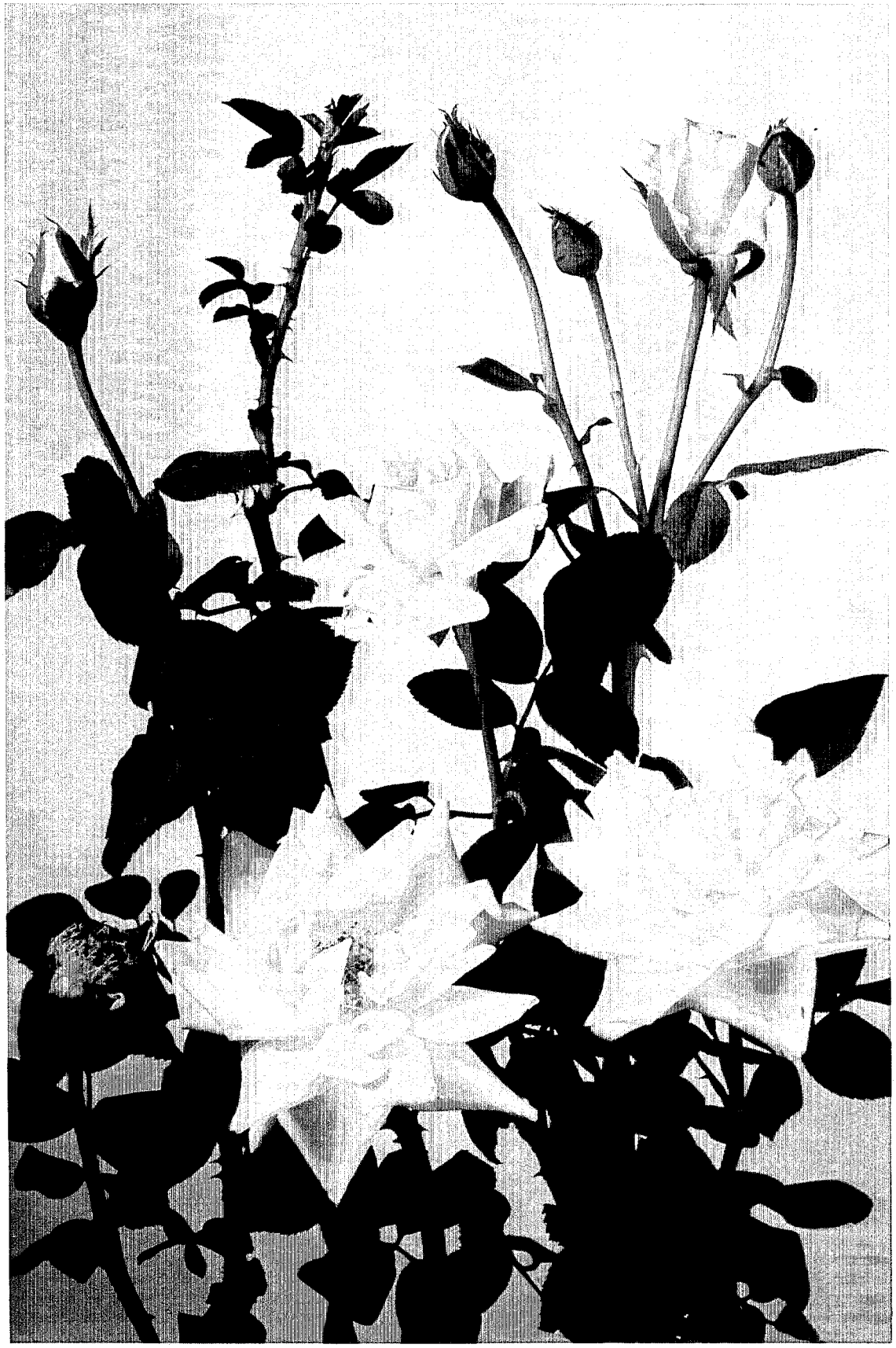

* * * * *